US006703367B1

(12) United States Patent
Garnick

(10) Patent No.: US 6,703,367 B1
(45) Date of Patent: Mar. 9, 2004

(54) METHODS FOR TREATING HOT FLASHES AND GYNAECOMASTIA

(75) Inventor: Marc B. Garnick, Brookline, MA (US)

(73) Assignee: Praecis Pharmaceuticals Inc., Waltham, MA (US)

( * ) Notice: Subject to any disclaimer, the term of this patent is extended or adjusted under 35 U.S.C. 154(b) by 0 days.

(21) Appl. No.: 09/674,132

(22) PCT Filed: Apr. 27, 2000

(86) PCT No.: PCT/US99/09081

§ 371 (c)(1),
(2), (4) Date: Feb. 16, 2001

(87) PCT Pub. No.: WO99/55358

PCT Pub. Date: Nov. 4, 1999

(51) Int. Cl.$^7$ .......................... A61K 38/09; C07K 7/23

(52) U.S. Cl. ...................... 514/15; 514/800; 530/313; 530/328

(58) Field of Search .................... 514/15, 800; 530/313, 530/328

(56) References Cited

U.S. PATENT DOCUMENTS

| | | | |
|---|---|---|---|
| 3,608,075 A | 9/1971 | Glen | 424/238 |
| 3,733,407 A | 5/1973 | Segre | 424/239 |
| 4,076,811 A | 2/1978 | Lachnit-Fixson et al. | 424/239 |
| 4,145,416 A | 3/1979 | Lachnit-Fixson et al. | 424/238 |
| 4,425,339 A | 1/1984 | Pitchford | 424/239 |
| 4,788,062 A | 11/1988 | Gale et al. | 424/449 |
| 4,826,831 A | 5/1989 | Plunkett et al. | 514/170 |
| 4,839,370 A * | 6/1989 | Hartmann et al. | 546/219 |
| 4,992,421 A | 2/1991 | De et al. | |
| 5,180,711 A | 1/1993 | Hodgen | 514/15 |
| 5,516,887 A * | 5/1996 | Deghenghi | 531/313 |
| 5,658,884 A | 8/1997 | Hodgen | 514/12 |
| 5,681,817 A | 10/1997 | Hodgen et al. | 514/12 |
| 5,824,286 A | 10/1998 | Hodgen | 424/9.1 |

FOREIGN PATENT DOCUMENTS

WO    WO 96/40757    *    6/1995

OTHER PUBLICATIONS

Large et al. Gynaecomastia Complicating the Treatment of Myeloma. British Journal of Cancer. 1983. Vol. 48. Pp. 69–74.*
Nagamani et al. Treatment of Menopausal Hot Flashes with Transdermal Adminstration of Clonidine. American Journal of Obstetrics and Gynecology. Mar. 1987. Vol. 156. No. 3. Pp. 561–565.*
Parra et al. Treatment of Post–Orchiectomy Hot Flashes with Transdermal Administration of Clonidine. The Journal of Urology. Apr. 1990. Vol. 143. Pp. 753–754.*
Database Medline on STN, US National Library of Medicine, (Bethesda, MD, USA), No. 95010461, Kronenberg. F. 'Hot Flashes: Phenomenology, Quality of Life, and Search for Treatment Options,' abstract, Experimental Gerontology, May–Aug. 1994.*
Styne, D.M. et al., "Treatment of true precocious puberty with a potent luteinizing hormone–releasing factor agonist: Effect on growth, sexual maturation, pelvic sonography, and the hypothalamic–pituitary–gonadal axis," *J. Clin. Endocrinol. Metab.*, 61(1):142–151 (Jul. 1985).
Schwingl, P.J. et al., "Risk factors for menopausal hot flashes," *J. Am. Coll. Obstet. Gynecol.*, 84(1):29–34 (Jul. 1994).
Tataryn, I.V. et al., "LH, FSH and skin temperature uring the menopausal hot flash," *J. Clin. Endocrinol. Metab.*, 49(1):152–154 (Jul. 1979).
Tataryn, I.V. et al., "Objective techniques for the assessment of postmenopausal hot flashes," *J. Am. Coll. Obstet. Gynecol.*, 57(3):340–344 (Mar. 1981).
Large et al., "Gynaecomastia complicating the treatment of myeloma," *British Journal of Cancer*, 48:69–74 (1983).
Database Medline on STN, US National Library of Medicine, (Bethesda, MD, USA) No. 95010461, Kronenberg. F. "Hot flashes: Phenomenology, quality of life, and search for treatment options," abstract, Experimental Gerontology, (1994).
Meldrum, D.R. et al., "Pituitary hormones during the menopausal hot flash," *J. Am. Coll. Obstet. Gynecol.*, 64(6):752–756 (Dec. 1984).
Meldrum, D.R. et al., "Gonadotropins, estrogens, and adrenal steroids during the menopausal hot flash," *J. Clin. Endocrinol. Metab.*, 50(4):685–689 (Dec. 1984).
Molnar, G.W., "Thyrotropin–releasing hormone and the menopausal hot flash," *Maturitas,*3(2):115–123 (Aug. 1981).
Moon, T.D., "Cyproterone acetate for treatment of hot flashes after orchiectomy," *J. Urol.*, 134(1):155–156 (Jul. 1985).
Nagamani, M. et al., "Treatment of menopausal hot flashes with transdermal administration of clonidine," *Am. J. Obstet. Gynecol.*, 156(3):561–565 (Mar. 1987).
Norcross, W.A. et al., "Hot flashes in men with testicular insufficiency," *West J. Med.*, 145(4):515–516 (Oct. 1986).

(List continued on next page.)

*Primary Examiner*—Brenda Brumback
*Assistant Examiner*—Anish Gupta
(74) *Attorney, Agent, or Firm*—Lahive & Cockfield, LLP; Giulio A. DeConti, Jr.; Maria Laccotripe-Zacharakis

(57) ABSTRACT

Methods to inhibit hot flashes or gynaecomastia in a subject are provided. In the methods of the invention, an LHRH antagonist is administered to a subject in need of treatment for hot flashes or gynaecomastia such that hot flashes or gynaecomastia are inhibited in the subject. In a particularly preferred embodiment, the invention provides a method for inhibiting menopause-related hot flashes in which an LHRH antagonist is administered to a subject in need of treatment for menopause-related hot flashes such that the hot flashes are inhibited in the subject.

17 Claims, No Drawings

OTHER PUBLICATIONS

Parra, R.O. et al., "Treatment of post–orchiectomy hot flashes with transdermal administration of clonidine," *J. Urol.,* 143(4):753–754 (Apr. 1990).

Quella, S. et al., "A qualitative approach to defining 'hot flashes' in men," *Urol. Nurs.,* 14(4):155–158 (Dec. 1994).

Saltiel, E. et al, "Pharmacologic management of endometriosis," *Clin. Pharm.,* 10(7):518–531 (Jul. 1991).

Scoccia, B. et al., "Pathological hyperprolactinemia suppresses hot flashes in menopausal women," *J. Clin. Endocrinol. Metab.,* 66(4):868–871 (1988).

Sharma, O.P. et al., "The gonadotropin–releasing hormone (GnRH) agonist–induced initial rise of bioactive LH and testosterone can be blunted in a dose–dependent manner by GnRH antagonist in the non–human primate," *Urol. Res.,* 20:317–321 (1992).

Smith, P.H., "Hormone therapy: An overview," *Cancer surveys* 23:171–181 (1995).

Steingold, K. et al., "Treatment of hot flashes with transdermal estradiol administration," *J. Clin. Endocrinol. Metab.,* 61(4):627–632 (Oct. 1985).

Steingold, K. et al., "Clinical and hormal effects of chronic gonadotropin–releasing hormone agonist treatment in polycystic ovarian disease," *J. Clin. Endocrinol. Metab.,* 65(4):773–778 (Oct. 1987).

Steingold, K. et al., "Treatment of endometriosis with a long–acting gonadotropin–releasing hormone agonist," *J. Am. Coll. Obstet. Gynecol.,* 69(3.1):403–411 (Mar. 1987).

Gambone, J. et al., "Further delineation of hypothalamic dysfunction responsible for menopausal hot flashes," *J. Clin. Endocrinol. Metab.,* 59(6):1097–1002 (Dec. 1984).

Garnick, M.B., "Prostate cancer: Screening, diagnosis, and management," *Annals of internal medicine,* 118:804–818 (May 1993).

Garnick, M. B., "The dilemmas of Prostate cancer," *Scientific American,* 270(4):72–81 (Apr. 1994).

Hands, L. J., et al., "Gynaecomastia," *Br. J. Surg.* 78:907–911 (Aug. 1991).

Hughes–Davies, T.H., "Megestrol acetate for the prevention of hot flashes," (Letter; comment), *N. Engl. J. Med.,* 332(1):64 (Jan. 1995).

Kronenberg, F., "Thermoregulatory physiology of menopausal hot flashes: A Review," *Can. J. Physiol. Pharmacol.,* 65(6):1312–1324 (Jun. 1987).

Kronenberg, F., "Hot flashes: Epidemiology and physiology," *Ann. N. Y. Acad. Sci.,* 592:52–86, 123–133 (1990).

Kronenberg, F. et al., "Menopausal hot flashes: thermoregulatory, cardiovascular, and circulating catecholamine and LH changes," *Maturitas.,* 6:31–43 (1984).

Labrie, F. et al., "Combination therapy for prostate cancer," *Cancer Supp.,* 71(3):1059–1067 Feb. 1993).

Laufer, L.R. et al., "Effect of clonidine on hot flashes in postmenopausal women," *J. Am. Coll Obstet. Gynecol.,* 60(5):583–586 (Nov. 1982).

Letassy, N.A. et al., "Nafarelin acetate: A gonadotropin–releasing hormone agonist for the treatment of endometriosis," *DICP,* 24(12):1204–1209 (Dec. 1990).

Levine–Silverman, S., "The menopausal hot flash: A procrustean bed of research," *J. Adv. Nurs.,* 14(11):939–949 (Nov. 1989).

Loprinzi, C.L. et al., "Transdermal clonidine for ameliorating post–orchiectomy hot flashes," *J. Urol.,* 151(3):634–646 (Mar. 1994).

Loprinzi, C.L., et al., "Megastrol acetate for the prevention of hot flashes," *The New England Journal of Medicine,* 331(6):347–352 (Aug. 1994).

McCoy, N. et al., "Relationships among sexual behavior, hot flashes, and hormone levels in perimenopausal women," *Arch. Sex. Behav.,* 14(5):385–394.

McGuffey, E.C., "Treating hot flashes," *American Pharmacy,* 35(1):14 (Jan. 1995).

Albright, D.L. et al., "Temporal patterns of hot flashes in natural and surgically–induced menopause," *Prog. Clin. Biol. Res.,* 341A:731–739 (1990).

Bressler, et al., "Use of clonidine to treat hot flashes secondary to leuprolide or goserelin," *Ann. Pharmacother.,* 27(2):182–185 (Feb. 1993).

Buchholz, N.P. et al., "Hot flashes after orchiectomy in treatment of prostate cancer; A serious side effect," *Z. Gerontol.,* 27(5):334–336 (Sep./Oct. 1994).

Cignarelli, M. et al., "Biophysical and endocrine–metabolic changes during menopausal hot flashes," *Gynecol. Obstet. Invest.,* 27(1):34–37 (1989).

DeFazio, J., et al, "Induction of hot flashes in premenopausal women treated with a long–acting GnRH agonist," *J. Clin. Endocrinol. Metab.,* 56(3):445–448 (1983).

DeFazio, J. et al., "The effects of naloxone on hot flashes and gonadotropin secretion in postmenopausal women," *J. Clin. Endocrinol. Metab.,* 58(3):578–581 (Mar. 1984).

De Voogt, H.J., "The position of cyproterone acetate (CPA), a steroidal anti–androgen, in the treatment of prostate cancer," *Prostate Suppl.* 4:91–95 (1992).

Erlik, Y. et al., "Estrogen levels in postmenopausal women with hot flashes," *J. Am. Coll. Obstet. Gynecol.,* 59(4):403–407 (Apr. 1982).

Foster, G.V. et al., "Hot flashes in postmenopausal women ameliorated by danazol," *Fertil. Steril.,* 43(3):401–404 (Mar. 1985).

Freedman, R.R. et al., "Core body temperature and circadian rhythm of hot flashes in menopausal women," *J. Clin. Endocrinol. Metab.,* 80(8):2354–2358 (Aug. 1995).

Frishman, G. N., "The hot flash: Pathophysiology and treatment," *Rhode Island Medicine,* 78:132–133 (May 1995).

\* cited by examiner

METHODS FOR TREATING HOT FLASHES AND GYNAECOMASTIA

This Application is a Natural Stage of International Application No. PCT/US99/09081, which claims priority from provisional application No. 09/067,140.

BACKGROUND OF THE INVENTION

Menopausal women frequently experience a variety of symptoms which have been attributed to estrogen deprivation due to ovarian failure. Occurring in up to 85% of menopausal women, the most common and most characteristic symptom of menopause is an episodic disturbance consisting of sudden flashing and perspiration, referred to as the "hot flash." Vasomotor hot flashes are also the most frequent side effect associated with the anti estrogen drug Tamoxifen, used in the treatment of breast cancer. Non-hormonal related causes of hot flashes also exist even though they are not very common. One example is a deficiency or low, level of alcohol dehydrogenase. People with such deficiency may, be particularly prone to flushing with alcohol intake. Other rare causes of hot flashes include carcinoid syndrome or pheochromocytoma.

Although hot flashes are most commonly treated by estrogen replacement therapy (orally, transdermally, or via an implant), some women cannot tolerate estrogen treatment. In addition, estrogen is usually not recommended for women with hormonally, sensitive cancers (e.g. breast cancer). Other options have been studied for the treatment of hot flashes, including steroids, alpha-adrenergic agonists, and beta-blockers, with varying degree of success. Progestins, like Megestrol acetate and Medroxyprgesterone, have been shown to reduce hot flashes to 25–85% and 75–100% respectively, but the long-term effects of progestin therapy have not been studied. It is possible that side effects like thromboembolic disorders, edema, weight gain, lipid changes, and death due to cardiovascular disease make the use of this treatment unattractive.

Central nor adrenergic activity is believed to play a a role in the initiation of hot flashes. Therefore, agents that inhibit the release of nor epinephrine have also been used to ameliorate hot flashes. CLONIDINE™ (administered transdermally) reduced the frequency and severity of hot flashes due to Tamoxifen, but the results for orally administered clonidine varied. Side effects associated with the clonidine treatment included drowsiness, constipation, orthostatic hypotension, dry mouth, headache, nausea, fatigue, and decreased libido. Medthyldopa was shown to decrease hot flashes by 30% but it was associated with fatigue, weakness, dizziness, and nausea. Mixed reports exist for the use of Naproxen beta-blockers. VERALIPRIDE™ and NAXOLONE™.

Gynaecomastia is the development of excess breast tissue in the male. There may be a physiological (puberty, aging) or a pathological (drugs, tumors, liver and renal failure, hormonal imbalances) basis to it. Whatever the aetiology, the ultimate cause of gynaecomastia is an increase in the estrogen: testosterone ratio. Surgical correction (mastectomy) is a common method of treatment, although a rather costly one. Recently, liposuction has also been used as a method of treatment. This method, however, does not completely cure true gynaecomastia, because it removes fat rather than breast tissue. Anti-estrogens have also been tried. Tamoxifen and DANAZOL™ have been shown to reduce gynaecomastia in approximately 70% of middle aged men (Parker L N et al. Metabolism, 1986, 35: 705–8. Jones D J et al, Ann Roy Coll Surg, 1990, 72:286–8). CLOMIPHENE™ proved to be unsuccessful and was associated with adverse side-effects (Ploudre P V et al, Am. J. Dis. Child., 1983, 137: 1080–2).

Accordingly, treatment methods are needed for patients suffering from hot flashes or gynaecomastia, which are effective and will not result in adverse side-effects.

SUMMARY OF THE INVENTION

This invention provides effective treatments for inhibiting hot flashes or gynaecomastia in subjects suffering from these disorders. In general, the treatment methods of the invention involve administering an LHRH antagonist to a subject suffering from, or at risk for suffering from, hot flashes or gynaecomastia such that the hot flashes or gynaecomastia are inhibited in the subject.

Thus, one aspect of the invention features a method of inhibiting hot flashes in a subject by administering an LHRH antagonist to the subject such that hot flashes are inhibited in the subject. In another embodiment, the invention provides a method of treating a subject for hot flashes in which a subject in need of treatment for hot flashes is first selected for treatment and then an LHRH antagonist is administered to the subject such that the subject is treated for hot flashes. The subject in need of treatment for hot flashes can be a subject currently suffering from hot flashes or a subject that is at risk for suffering from hot flashes. In an especially preferred embodiment, the invention provides a method of treating a subject for menopause-related hot flashes. In this method, a subject in need of treatment for menopause-related hot flashes is selected and an LHRH antagonist is administered to the subject such that the subject is treated for menopause-related hot flashes. The subject in need of treatment for menopause-related hot flashes can be a subject currently suffering from menopause-related hot flashes or a subject at risk for suffering from menopause-related hot flashes. In addition to treatment for menopause-related hot flashes, the methods of the invention can be used to treat hot flashes that result from other disorder or treatments, such as hot flashes that are the result of prostate cancer treatment, tamoxifen acetate treatment, alcohol dehydrogenase deficiency or carcinoid syndrome/pheochromocytoma.

Another aspect of the invention pertains to a method of inhibiting gynaecomastia in a subject by administering an LHRH antagonist to the subject such that gynaecomastia is inhibited in the subject. In another embodiment, the invention provides a method of treating a subject for gynaecomastia in which a subject in need of treatment for gynaecomastia is first selected for treatment and then an LHRH antagonist is administered to the subject such that the subject is treated for gynaecomastia. The subject in need of treatment for gynaecomastia can be a subject currently suffering from gynaecomastia or a subject that is at risk for suffering from gynaecomastia. In a preferred embodiment, gynaecomastia in the subject is the result of a hormonal balance.

Any LHRH antagonist that effectively inhibits the activity of the LHRH-R receptor can be used in the methods of the invention. However, in a particularly preferred embodiment, the LHRH antagonist has the structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH (referred to herein as PPI-149).

In another preferred embodiment of the invention, the subject is a mammal, e.g., most preferably a human.

In yet another preferred embodiment, the LHRH antagonist is administered to the subject by a parenteral route, preferably by injection, most preferably by intramuscular or subcutaneous/intradermal injection.

In still another preferred embodiment, the LHRH antagonist is administered to the subject in a pharmaceutically acceptable formulation. The pharmaceutically acceptable formulation can be a dispersion system. For example, the formulation can be lipid-based (e.g., a liposome formulation) or polymer-based (e.g., a polymeric microsphere). In a particularly preferred embodiment, the formulation comprises the LHRH antagonist in an insoluble complex with an anionic carrier macromolecule (e.g., carboxymethylcellulose).

In preferred embodiments, the LHRH antagonist is administered at, for example, a dosage of about 15–300 μg/kg/day, 15–200 μg/kg/day or 15–100 μg/kg/day. The LHRH antagonist can be administered continuously using a sustained-release formulation, e.g., a formulation in an osmotic pump or a formulation that allows for slow-release of the LHRH antagonist into the tissue of the subject. For sustained treatment of a subject, the LHRH antagonist can be administered to the subject for at least one month, preferably three and more months and even more preferably six months. To achieve sustained treatment for extended periods of time, it may be necessary to readminister a sustained release formulation. For example, a sustained release formulation that delivers the LHRH antagonist for a period of one month can be readministered on a monthly basis to achieve sustained treatment for several months (e.g., 6 months). Similarly, a sustained release formulation that delivers the LHRH antagonist for a period of one week can be readministered on a weekly basis to achieve sustained treatment for several weeks. The sustained release formulations provided herein (see e.g., Example 3) can deliver an LHRH antagonist for a period of at least about one month and thus can be readministered on a monthly basis to achieve extended treatment.

The LHRH antagonist can be administered to the subject alone or in combination with at least one other therapeutic agent. Examples of other therapeutic agents that may be administered with the LHRH antagonist include LHRH agonists, antiandrogens, antiestrogens and inhibitors of sex steroid biosynthesis.

In another embodiment, the LHRH antagonist is administered in combination with a sex hormone, such as estrogen or testosterone. For example, estrogen replacement therapy is often used during (and after) menopause to reduce certain symptoms associated with menopause and thus one in embodiment of the invention, a subject is treated with both estrogen (and/or other related female sex hormone(s), such as progesterone) and an LHRH antagonist. The use of an LHRH antagonist in combination with the estrogen (and/or other related female sex hormone(s)) may allows for the us of lower dosages of the hormone than when the hormone is used alone. Similar combination therapy can be used in disorders where testosterone (and/or other related male sex hormone(s)) is administered.

Other features and advantages of the invention will be apparent from the following detailed description, and from the claims.

DETAILED DESCRIPTION OF THE INVENTION

The present invention provides a method of inhibiting hot flashes or gynaecomastia in a subject. The methods of the invention generally feature administering an LHRH antagonist to a subject such that hot flashes or gynaecomastia are inhibited in the subject. In certain embodiments, the methods of the invention involve selecting a subject in need of treatment for hot flashes or gynaecomastia and administering an LHRH antagonist to the subject such that the subject is treated for hot flashes or gynaecomastia. The methods of the invention for treating hot flashes can be used to treat hot flashes that result from, for example, menopause, tamoxifen acetate treatment, prostate cancer treatment, alcohol dehydrogenase deficiency, or carcinoid syndrome/pheochromocytoma. The methods of the invention or treating gynaecomastia can be used to treat gynaecomastia that results from, for example, a hormone imbalance.

Although the exact pathophysiology of the hot flash is unknown it appears to be related to an alteration in the set point of the thermoregulatory center located in the hypothalamus. Blood sampling in women experiencing hot flashes, has documented that the onset of a hot flash is correlated with the release of gonadotropin releasing hormone (GnRH) in the hypothalamus, and a subsequent luteinizing hormone (LH) pulse. This rise in the levels of LH is thought to cause a decrease in the set point of the thermoregulatory center. In an attempt to restore equilibrium, a hot flash is produced. Although not intending to be limited by mechanism, the ability of the LHRH antagonists of the invention to inhibit hot flashes is thought to result, at least in part, from its inhibition of the LH pulse that decreases the set point of the thermoregulatory center.

As used herein, the term "LHRH antagonists", refers to a compound that inhibits the luteinizing hormone releasing hormone receptor, such that release of luteinizing hormone is inhibited. The term "LHRH antagonist" may be used interchangeably with the term "LHRH-R antagonist" to refer to compounds that inhibit LHRH-R such that release of LH is inhibited. LHRH antagonists have been described in the art: see e.g., U.S. Pat. No. 5,470,947 to Folklers et al.; Folkers et al., U.S. Pat. No. 5,843,901 to Roeske et al.; U.S. Pat. No. 5,413,990 to Haviv; U.S. Pat. No. 5,300,492 to Haviv; U.S. Pat. No. 5,371,070 to Koerber et al.; U.S. Pat. No. 5,296,468 to Hoeger et al.; U.S. Pat. No. 5,171,835 to Janaky et al.; U.S. Pat. No. 5,003,011 to Coy et al.; U.S. Pat. No. 4,431,635 to Coy; U.S. Pat. No. 4,992,421 to De et al.; U.S. Pat. No. 4,851,385 to Roeske; U.S. Pat. No. 4,801,577 to Nestor, Jr. et al.; and U.S. Pat. No. 4,689,396 to Roeske et al.

For example, preferred LHRH-R antagonists which can be used in the methods of the invention include peptides comprising a structure:

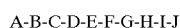

wherein
    A is pyro-Glu, Ac-D-Nal, Ac-D-Qal, Ac-Sar, or Ac-D-Pal
    B is His or 4-Cl-D-Phe
    C is Trp, D-Pal, D-Nal, L-Nal-D-Pal(N—O), or D-Trp
    D is Ser
    E is N-Me-Ala, Tyr, N-Me-Tyr, Ser, Lys(iPr), 4-Cl-Phe, His, Asn, Met, Ala, Arg or Ile,
    F is

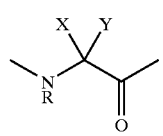

wherein
    R and X are independently H or alkyl; and
    Y comprises a dipolar moiety;

G is Leu or Trp;

H is Lys(iPr), (Gln, Met, or Arg

I is Pro; and

J is Gly-NH$_2$ or D-Ala-NH$_2$;

or a pharmaceutically acceptable salt thereof In preferred embodiments, Y is selected from the group consisting of ylids, tertiary amine oxides, nitrile oxides, pyridine-N-oxides, and pyridinium zwitterions. In particularly preferred embodiments, Y is all lid, a pyridine-N-oxide or a pyridinium zwitterion. In a preferred embodiment, the peptide comprises a structure:

Ac-D-Nal-4-Cl-D-Phe-D-Pal-Ser-Tyr-D-Pal(N—O)-Leu-Lys(iPr)-Pro-D-Ala-NH$_2$;

In another preferred embodiment, the peptide comprises a structure:

Ac-D-Nal-4-Cl-D-Phe-D-Pal-Ser-Tyr-D-Pal(CH$_2$COO$^-$)-Leu-Lys(iPr)-Pro-Ala-NH$_2$;

or a pharmaceutically acceptable salt thereof.

In another aspect, an LHRH-R antagonist used in the methods of the invention includes a peptide comprising a structure:

A-B-C-D-E-F-G-H-I-J wherein

A is pyro-Glu, Ac-D-Nal, Ac-D-Qal, Ac-Sar, or Ac-D-Pal

B is His or 4-Cl-D-Phe

C is Trp, D-Pal, D-Nal, L-Nal-D-Pal(N—O), or D-Trp

D is Ser

E is N-Me-Ala, Tyr, N-Me-Tyr, Ser, Lys(iPr), 4-Cl-Phe, His, Asn, Met, Ala, Arg or Ile;

F is D-Arg, D-Lys(iPr), D-Pal(iPr), D-Cit or Q, wherein Q has a structure

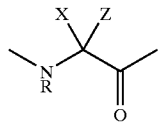

wherein

R and X are, independently, H or alkyl; and

Z comprises a cationic moiety selected from the group consisting of cationic pyridinium moieties and sulfonium moieties, with the proviso that the cationic moiety is not N-methyl pyridinium;

G is Leu or Trp;

H is Lys iPr), Gln, Met, Arg or Q;

I is Pro; and

J is Gly-NH$_2$ or D-Ala-NH$_2$;

with the proviso that at least one of F and H is Q;

or a pharmaceutically acceptable salt thereof.

In preferred embodiments, F is Q and Z is a cationic pyridinium moiety. In preferred embodiments, Z is an N-benzyl pyridinium moiety. In other preferred embodiments, F is Q and Z is a sulfonium moiety. In yet other preferred embodiments, H is Q and Z is a sulfonium moiety. In a particularly preferred embodiment, the peptide comprises a structure Ac-Sar4-Cl-D-Phe-D-Nal-Ser-Tyr-D-Pal(Bzl)-Leu-Lys(iPr)-Pro-Ala-NH$_2$;

or a pharmaceutically acceptable salt thereof. In another particularly preferred embodiment, the peptide comprises a structure:

Ac-D-Nal4-Cl-D-Phe-D-Trp-Ser-Tyr-D-Met(S$^+$Me)-Leu-Arg-Pro-Ala-NH$_2$;

or a pharmaceutically acceptable salt thereof. In a particularly preferred embodiment, the peptide comprises a structure:

Ac-D-Nal4-Cl-D-Phe-D-Pal-Ser-Tyr-D-Arg-Leu-Met(S$^+$Me)-Pro-Ala-NH$_2$;

or a pharmaceutically acceptable salt thereof.

In another aspect, an LHRH-R antagonist used in the methods of the invention includes a peptide comprising a structure:

A-B-C-D-E-F-G-H-I-J wherein

A is p-Glu, Ac-D-Nal, Ac-D-Qal, Ac-Sar, or Ac-D-Pal

B is His or 4-Cl-D-Phe

C is Trp, D-Pal, D-Nal, L-Nal-D-l-Pal(N—O), or D-Trp

D is Ser

F is N-Me-Ala, Tyr, N-Me-Tyr, Ser, Lys(iPr), 4-Cl-Phe, His, Asn, Met, Ala, Arg or Ile;

F is

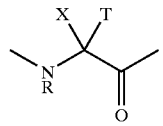

wherein

R and X are, independently, H or alkyl; and

T comprises a receptor-modifying moiety;

G is leu or Trp;

H is Lys(iPr), Gin, Met, or Arg

I is Pro; and

J is Gly-NH$_2$ or D-Ala-NH$_2$;

or a pharmaceutically acceptable salt thereof.

In preferred embodiments, T is selected from the group consisting of ylids, sulfonium moieties, α-halocarbonyis, sulfates, sulfonates, alkly halides and benzyl halides. In a particularly preferred embodiment, T is an α-halocarbonyl.

In another embodiment, an LHRH-R antagonist used in the methods of the invention includes a peptide comprising a structure:

A-B-C-D-E-F-G-H-I-J wherein

A is pyro-Glu, Ac-D-Nal, Ac-D-Qal, Ac-Sar, or Ac-D-Pal

B is His or 4-Cl-D-Phe

C is Trp, D-Pal, D-Nal, L-Nal-D-Pal(N—O), or D-Trp

D is Ser

E is N-Me-Ala, Tyr, N-Me-Tyr, Ser, Lys(iPr), 4-Cl-Phe, His, Asn, Met, Ala, Arg or Ile;

F is

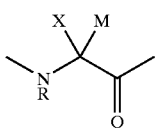

wherein
R and N are, independently, H or alkyl; and
M comprises an N-acyl hydrophilic moiety;
G is Leu or Trp;
H is Lys(iPr), Gln, Met, or Arg
I is Pro; and
J is Gly-NH$_2$ or D-Ala-NH$_2$;
or a pharmaceutically acceptable salt thereof In another aspect, an LHRH-R antagonist used in the methods of the invention includes a peptide comprising a structure:

A-B-C-D-E-F-G-H-I-J wherein
A is pyro-Glu, Ac-D-Nal, Ac-D-Qal, Ac-Sar, or Ac-D-Pal
B is His or 4-Cl-D-Phe
C is Trp, D-Pal, D-Nal, L-Nal-D-Pal(N—O), or D-Trp
D is Ser
E is N-Me-Ala, Tyr, N-Me-Tyr, Ser, Lys(iPr), 4-Cl-Phe, His, Asn, Met, Ala, Arg or Ile;
F is

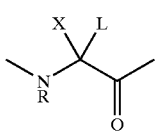

wherein
R and X are, independently, H or alklyl; and
L comprises a small polar moiety;
G is Leu or Trp;
H is Lys(iPr), Gin, Met, or Arg
I is Pro; and
J is Gly-NH$_2$ or D-Ala-NH$_2$;
or a pharmaceutically acceptable salt thereof.

In preferred embodiments, L is selected from the group consisting of D-Cit, D-Asn, D-Gln, and D-Thr.

Preferred LHRH antagonists are those having good LHRH antagonist activity and low histamine-releasing activity (e.g., an ED$_{50}$ for histamine release in a standard in vitro histamine release assay of at least 3 µg/ml, more preferably at least 5 µg/ml, and still more preferably at least 10 µg/ml) and that exhibit water solubility. The efficacy of candidate LHRH antagonists in inhibiting LH release can be assayed, for example, in an animal model such as that described in Corbin and Beattie, *Endocrine Res. Commun.* 2:1 (1975). In this assay, the LHRH antagonistic activity of a candidate compound is assayed by measuring the antiovulatory activity (AOA) of the compound in rats. Preferably, histamine-releasing activity is assayed by the method described in U.S. Pat. No. 4,851,385 to Roeske. Preferred LHRH antagonists with low histamine-releasing activity and water solubility include compounds disclosed in PCT Publication WO 96/40757, the entire contents of which are expressly incorporated herein by reference. An especially preferred LHRH antagonist comprises the structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH (referred to as PPI-149 and described further in U.S. Pat. No. 5,843.901).

Alternatively, the methods of the invention can be used with any of a variety of compounds known in the art to have LHRH antagonist activity. These LHRH antagonists typically are analogues of the LHRH decapeptide, non-limiting examples of which include Antide, Nal-Glu (having the structure: Ac-D-Nal(2)$^1$, 4-Cl-D-Phe$^2$, D-Pal$^3$, Arg$^5$, D-Glu$^6$ (AA), D-Ala$^{10}$-LHRH) and SB-75 (also known as CETRORELIX™) (having the structure: Ac-D-Nal$^1$, 4-Cl-D-Phe$^2$, D-Pal$^3$, D-Cit$^6$, D-Ala$^{10}$-LHRH). Another example of an LHRH antagonist that can be used in the method of the invention has the structure: Ac-D-Nal$^1$, 4-Cl-D-Phe$^2$, D-Pal$^3$, N-Me-Tyr$^5$, D-Lys(N-epsilon-nicotinoyl)$^6$, Lys(iPr)$^8$, D-Ala$^{10}$-LHRH (described further in European Patent EP 400 065 B).

As used herein, the term "inhibiting" (as in "inhibiting hot flashes" or "inhibiting gynaecomastia") is intended to mean reducing or downregulating hot flashes or gynaecomastia. The term "inhibiting" is intended to include both partial and complete inhibition.

As used herein, the term "treating" refers to exposing a subject to a specific therapeutic regimen for the purpose of relieving a symptom, or preventing a particular condition.

As used herein, the term "subject" is intended to include animals susceptible to hot flashes and/or gynaecomastia, preferably mammals, most preferably humans. In a preferred embodiment, the subject is a primate. In an even more preferred embodiment, the primate is a human. Other examples of subjects include dogs, cats, goats, and cows.

The term "hot flash" is an art recognized term that refers to an episodic disturbance in body temperature typically consisting of a sudden elevation in body temperature, usually with accompanied perspiration in a subject.

As used herein, the term "anti-estrogen", refers to compounds that antagonize the release or action of estrogens. Antiestrogens are known in the art (e.g., tamoxifen and derivatives thereof, such as trioxifene, toremifene and droloxifene) and are commercially available (e.g., tamoxifen; trade name: NOLVADEX™, a product of ICI Pharmaceuticals).

As used herein, the term "anti-androgen" refers to a compound that antagonizes the release or action of androgens. Anti-androgens are known in the art (see. e.g., U.S. Pat. No. 4,386,080), and are commercially available (e.g., ANDORCUR™, a product of Schering A. G.) and include steroidal and nonsteroidal anti-androgens. Specific examples of nonsteroidal antiandrogens include flutamide (4'-nitro-3'-trifluorormethyl isobutyranilide; trade name EULEXIN™; Schering-Plough), bicalutamide and nilutamide.

As used herein, the term "LHRH agonist" refers to a compound that stimulates the luteinizing hormone releasing hormone receptor such that luteinizing hormone is released (e.g., a compound that mimics the activity of LHRH). An LHRH agonist can have greater LH-releasing activity than natural LHRH (referred to as a "superagonist"). Many LHRH agonists and superagonist are known in the art. Commercially available LHRH agonists include leuprolide (trade name: LUPRON™ Abbott/TAP), goserelin (trade name: ZOLADEX™; Zeneca), buserelin (Hoechst), triptorelin (also known as Decapeptyl, D-Trp-6-LHRH and DEBIOPHARM™; Ipsen/Beaufour), nafarelin (trade name" SYNAREL™; Syntex), lutrelin (Wyeth), cystorelin (Hoechst), gonadorelin (Ayerst) and histrelin (Ortho).

The term "inhibitor of sex steroid biosynthesis" is intended to include inhibitors of adrenal sex steroid biosynthesis (e.g., aminoglutethimide) and inhibitors of testicular sex steroid biosynthesis (e.g., ketoconazole), or combinations thereof.

Pharmaceutically Acceptable Formulations

In the methods of the invention, the LHRH antagonist typically is administered in a pharmaceutically acceptable formulation. The pharmaceutically acceptable formulations of the invention typically contain the LHRH antagonist and a pharmaceutically acceptable carrier and are intended to include any formulation compatible with pharmaceutical administrations, including, for example, synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In a particularly preferred embodiment, the pharmaceutical formulation comprises an LHRH antagonist (preferably having the structure Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH) in a water-insoluble complex with a carrier macromolecule, preferably an anionic polymer such as carboxymethylcellulose, as described in U.S. application Ser. No. 08/762,747 and corresponding PCT Application No. PCT/US97/22881, the contents of both of which are expressly incorporated herein by reference. In brief, the complex of the LHRH antagonist and a carrier macromolecule is formed by combining the LHRH antagonist and the carrier macromolecule under conditions such that a substantially water-insoluble complex is formed, e.g., aqueous solutions of the LHRH antagonist and carrier macromolecule are mixed until the complex precipitates. The complex may be in the form of a solid (e.g., a paste, granules, a powder or a lyophilizate) or the powdered form of the complex can be pulverized finely enough to form stable liquid suspensions or semi-solid dispersions. The complex is suitable for sterilization, such as by gamma irradiation or electron beam irradiation, prior to administration in vivo. Preferred carrier macromolecules for use in the complex are anionic polymers, such as anionic polyalcohol derivatives, or fragments thereof, and salts thereof (e.g., sodium salts). Anionic moieties with which the polyalcohol can be derivatized include, for example, carboxylate, phosphate or sulfate groups. A particularly preferred anionic polymer is an anionic polysaccharide derivative, or fragment thereof, and salts thereof (e.g., sodium salts). The carrier macromolecule may comprise a single molecular species (e.g., a single type of polymer) or two or more different molecular species (e.g., a mixture of two types of polymers). Examples of specific anionic polymers include carboxymethylcellulose, algin, alginate, anionic acetate polymers, anionic acrylic polymers, xantham gums, sodium starch glycolate, and fragments, derivatives and pharmaceutically acceptable salts thereof, as well as anionic carageenan derivatives, anionic polygalacturonic acid derivatives, and sulfated and sulfonated polystyrene derivatives. A preferred anionic polymer is carboxymethylcellulose sodium salt. In certain embodiments, the carrier macromolecule, preferably carboxymethylcellulose sodium, and the LHRH antagonist, preferably PPI-149, are combined at a ratio of 0.2:1 (w/w) of carrier macromolecule:peptidic compound. In various other embodiments, the ratio of carrier macromolecule to peptidic compound (w/w) can be, for example, 0.5:1, 0.4:1, 0.3:1, 0.25:1, 0.15:1 or 0.1:1. In other preferred embodiments, the peptide content of the solid ionic complex of the LHRH antagonist and the carrier macromolecule is 57%, 60%, 65%, 70%, 75%, 79%, or more by weight. In yet other preferred embodiments, the peptide content of the solid ionic complex of the LHRH antagonist and the carrier macromolecule is 57 to 79% by weight. This formulation of the LHRH antagonist and a carrier macromolecule has the additional advantage that it provides sustained delivery of the LHRH antagonist into the tissue of the subject to which it is administered.

In another embodiment, the pharmaceutically acceptable formulation comprises polymeric matrix The terms "polymer" or "polymeric" are art-recognized and include a structural framework comprised of repeating monomer units. The terms also include co-polymers and homopolymers e.g., synthetic or naturally occurring. Linear polymers, branched polymers, and cross-linked polymers are also meant to be included. For example, polymeric materials suitable for forming the pharmaceutically acceptable formulation employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, and pluronics. These polymers are biocompatible, biodegradable without producing any toxic byproducts of degradation, and they possess the ability to modify the manner and duration of LHRH antagonist release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection.

Polymers can be prepared using methods known in the art (Sandier, S. R.; Karo, W. *Polymer Syntheses:* Harcourt Brace: Boston, 1994; Shalaby, W.; Ikada, Y.; Langer, R.; Williams, J. *Polymers of Biological and Biomedical Significance* (ACS Symposium Series 540; American Chemical Society: Washington, D.C., 1994). Polymers can be designed to be flexible; the distance between the bioactive side-chains and the length of a linker between the polymer backbone and the group can be controlled. Other suitable polymers and methods for their preparation are described in U.S. Pat. No. 5,455,044 and 5,576,018.

The polymeric formulations can be formed, for example, by dispersion of the active ingredient (e.g., the LHRH antagonist) within liquefied polymer, as described in U.S. Pat. No. 4,883,666, or by such methods as bulk polymerization, interfacial polymerization, solution polymerization and ring polymerization as described in Odian G., Principles of Polymerization and ring opening polymerization, 2nd ed., John Wiley & Sons, New York, 1981. The properties and characteristics of the formulations are controlled by, varying such parameters as the reaction temperature, concentrations of polymer and LHRH antagonist, types of solvent used, and reaction times.

The LHRH antagonist can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two.

In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or "MLV"), unilamellar liposomes, including small unilamellar liposomes (also known as unilamellar vesicles or "SUV") and large unilamellar liposomes (also known as large unilamellar vesicles or "LUV"), can all be used so long as a sustained release rate of the encapsulated LHRH antagonist can be established. In one embodiment, the lipid-based formulation can be a multivesicular liposome system. Methods of making controlled release multivesicular liposome drug delivery systems are described in Applications WO 9513796 and WO 9703652.

The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidyglycerol are used.

In preparing lipid-based vesicles containing an LHRH antagonist, such variables as the efficiency of the LHRH antagonist encapsulation, lability of the LHRH antagonist, homogeneity and size of the resulting population of vesicles, LHRH antagonist-to-lipid ratio, permeability, instability of the preparation, and pharmaceutical acceptability of the formulation should be considered (see Szoka, et al., *Annual Reviews of Biophyics and Bioengineering*, 9:467, 1980; Deamer, et al., in *Lipidsomes*, Marcel Dekker, New York, 1983, 27; and Hope, et al., *Chem. Phys. Lipids*, 40:89, 1986).

Other formulations include controlled-release compositions (as referred to as "sustained release formulations") such as are known in the art for the administration of leuprolide (trade name: Lupron®), e.g., microcapsules (U.S. Pat. Nos. 4,652,441 and 4,917,893), injectable formulations (U.S. Pat. No. 4,849,228), lactic acid-glycolic acid copolymers useful in making microcapsules or injectable formulations (U.S. Pat. No. 4,677,191 and 4,728,721), and sustained-release compositions for water-soluble polypeptides (U.S. Pat. No. 4,675,189). A particularly preferred sustained release formulation comprises the LHRH antagonist in a water-insoluble complex with an anionic carrier macromolecule (described further above and in U.S. application Ser. No. 08/762,747 and PCT Application PCT/US97/22881).

In addition to the LHRH antagonist and a pharmaceutically acceptable carrier, the pharmaceutically acceptable formulation used in the method of the invention can comprise additional pharmaceutically acceptable reagents and/or excipients. As used herein, "pharmaceutically acceptable reagent and/or excipient" is intended to include any and all solvents, dispersion media, coatings, antibacterial and antifungal agents, isotonic agents (e.g., sugars, polyalcohols such as mannitol, sorbitol, or sodium chloride) and absorption delaying agents (e.g., monostearate salts and gelatin), and the like that are physiologically compatible. Excipients include pharmaceutically acceptable stabilizers and disintegrants. The proper fluidity can be maintained, for example, by the use of a coating such as lecithin, by the maintenance of the required particle size in the case of dispersion and by the use of surfactants. Except insofar as any conventional media or agent is incompatible with the active compound (e.g., the LHRH antalonist) use there of in the pharmaceutical compositions of the invention is contemplated.

Administration of the Pharmaceutically Acceptable Formulation

The LHRH antagonist can be administered as needed to a subject and preferably is administered continuously using a sustained-release formulation, such as a formulation comprising a water-insoluble complex of the LHRH antagonist and an anionic carrier macromolecule, a slow-release polymer (e.g., a poly-lactide polymer, a poly-glycolide polymer and a poly-lactide/poly-glycolide copolymer), a formulation in an osmotic pump, an implant or a transdermal patch. The sustained release formulation is administered by an appropriate route for continual release of the drug in the subject, such as subcutaneous injection or implantation. The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization, described in U.S. Pat. No. 436,742. For injection, the LHRH antagonist formulation can be formulated in liquid solutions, preferably in physiologically compatible buffers such as Hank's solution or Ringer's solution. In addition, the LHRH antagonist formulation may be formulated in solid form, e.g., lyophilized, and re-dissolved or suspended immediately prior to use. The injection can be, for example, in the form of a bolus injection or continuous infusion (e.g., using infusion pumps) of the LHRH antagonist formulation.

When appropriately formulated, an LHRH antagonist may be orally administered, for example, with an inert diluent or an assimilable edible carrier. The LHRH antagonist (and other ingredients) may also be enclosed in a hard or soft shell gelatin capsule, compressed into tablets, or incorporated directly into the subject's diet. For oral therapeutic administration, the LHRH antagonist may be incorporated with excipients and used in the form of ingestible tablets, buccal tablets, troches, capsules, elixirs, suspensions, syrups, wafers, and the like. The percentage of the LHRH antagonist in the compositions and preparations may, of course, be varied. The amount of the LHRH antagonist in such therapeutically useful compositions is such that a suitable dosage will be obtained.

To administer an LHRH antagonist by other than parenteral administration, it may be necessary to coat the compound with, or co-administer the compound with, a material to prevent its inactivation.

In one embodiment of the methods of the invention, an LHRH antagonist (typically in a pharmaceutical formulation) alone is administered to the subject. In another embodiment, the methods of the invention can involve administration of an LHRH antagonist in combination with one or more other therapeutic agents. Examples of other therapeutic agents, which can be combined with the LHRH antagonist treatment include antiestrogens (e.g., used in treatment of estrogen-dependent tumors, or in the treatment of gynaecomastia), anti-androgens, LHRH agonists or inhibitors of sex steroid biosynthesis. When an inhibitor of adrenal sex steroid biosynthesis is employed, it may be desirable to simultaneously administer hydrocortisone to the patient in an amount sufficient to maintain normal glucocorticoid levels.

Duration and Levels of Administration

In another embodiment of the invention, the pharmaceutically acceptable formulation provides sustained delivery, e.g., "slow release" of the LHRH antagonist to a subject. Preferably, the formulation provides sustained delivery of the LHRH antagonist for at least one week, more preferably at least two weeks and even more preferably at least one month after the pharmaceutically acceptable formulation is administered to the subject. In various embodiments, a subject may be treated for at least one month, at least three months or at least six months with the LHRH antagonist.

As used herein, the term "sustained delivery" is intended to include continual delivery of an LHRH antagonist in vivo over a period of time following administration. Sustained delivery of the LHRH antagonist can be demonstrated by, for example, the continued therapeutic effect of the LHRH antagonist over time (e.g., sustained delivery of the LHRH antagonist can be demonstrated by continued suppression of hot flashes or gynaecomastia over time). Alternatively, sustained delivery of the LHRH antagonist may be demonstrated by detecting the presence of the LHRH antagonist in vivo over time.

The pharmaceutical formulation, used in the method of the invention, contains a therapeutically effective amount of the LHRH antagonist. A "therapeutically effective amount" refers to an amount effective, at dosages and for periods of time necessary, to achieve the desired result. A therapeutically effective amount of the LHRH antagonist may vary according to factors such as the disease state, age, and weight of the subject, and the ability of the LHRH antagonist (alone or in combination with one or more other therapeutic agents) to elicit a desired response in the subject. Dosage regimens may be adjusted to provide the optimum therapeutic response. A therapeutically effective amount is also one in which any toxic or detrimental effects of the LHRH antagonist are outweighed by the therapeutically beneficial effects. A non-limiting range for a therapeutically effective amount of an LHRH antagonist is 0.01 $\mu$g/kg–10 mg/kg, preferably between about 0.01 and 5 mg/kg. In preferred embodiments, the dosage of LHRH antagonist is about 15–300 $\mu$g/kg/day, more preferably about 15–200 $\mu$g/kg/day and even more preferably about 15–100 $\mu$g/kg/day. Preferred dosages include 30 $\mu$g/kg/day, 50 $\mu$g/kg/day, or 100 $\mu$g/kg/day. It is to be noted that dosage values may vary with the severity of the condition to be alleviated. It is to be further understood that for any particular subject, specific dosage regimens should be adjusted over time according to the individual need and the professional judgment of the person administering or supervising the administration of the LHRH antagonist and that dosage ranges set forth herein are exemplary only and are not intended to limit the scope or practice of the claimed invention.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. "Dosage unit form" as used herein refers to physically discrete units suited as unitary dosages for the mammalian subjects to be treated, each unit containing a predetermined quantity of the LHRH antagonist calculated to produce the desired therapeutic effect in association with the required pharmaceutical carrier. The specification for the dosage unit forms of the invention are dictated by and directly dependent on (a) the unique characteristics of the specific LHRH antagonist used and the particular therapeutic effect to be achieved, and (b) the limitations inherent in the art of compounding such an LHRH antagonist for the treatment of hot flashes or gynaecomastia in a subject.

This invention is further illustrated by the following examples which should not be construed as limiting. The contents of all references, patents and published patent applications cited throughout this application are hereby incorporated by reference.

EXAMPLES

Example 1

In this example, patients with stage D1 or D2 metastatic prostate cancer or patients with a rising Prostate Specific Antigen (PSA) level after radiation therapy, radical prostatectomy, or other local therapy were treated with the LHRH antagonist PPI-149 at a dosage of either 30 mg/kg/day or 50 mg/kg/day for a sustained period of time (e.g., 14 or 28 days). Other patients were treated with the LHRH agonist leuprolide or with both PPI-149 and leuprolide.

During the course of treatment, patients were asked to fill out an endocrine-related questionnaire, which probed symptoms related to changes in androgenic hormone levels, including the occurrence of hot flashes. (Other symptoms probed included tiredness, loss of sexual desire, loss of sexual potency, smaller testicle size, changes or thinning in body hair, decrease in muscle mass, decrease in muscle tone, increase or decrease in body weight, urine frequency, urine urgency, urine hesitancy, and nocturia.) A summary of the results for the occurrence of hot flashes in patients treated with either PPI-149 alone, leuprolide alone or PPI-149 in combination with leuprolide are summarized below:

| Treatment Regimen | Occurence of Hot Flashes |
| --- | --- |
| PPI-149 alone | 0/8 |
| Leuprolide alone | |
| PPI-149 + Leuprolide | 3/8 |

This data demonstrates that patients treated with the LHRH antagonist PPI-149 alone did not experience hot flashes whereas more than half of the patients treated with the LHRH agonist leuprolide experienced hot flashes. Although not intending to be limited by mechanism, it is thought that the occurrence of hot flashes results, at least in part, from fluctuations in the levels of circulating luteinizing hormone (LLH) and/or follicle stimulating hormone (FSH) and, accordingly, that use of an LHRH antagonist (which inhibits the activity of the LHRH receptor without causing minor surges in the levels of LH and/or FSH associated with the use of an LHRH agonist) can serve to avoid or inhibit these fluctuations in LH and/or FSH levels wherever the), may occur clinically (e.g., in menopausal or postmenopausal women experiencing hot flashes or other patient population experiencing hot flashes).

Example 2

Patients with stage D1 or D2 metastatic prostate cancer or patients with a rising Prostate Specific Antigen (PSA) level after radiation therapy, radical prostatectomy, or other local therapy, that were undergoing treatment with the LHRH antagonist PPI-149 as described in Example 1, were questioned as to the occurrence of gynaecomastia. These results were compared to data obtained for patients treated with the LHRH agonist Leuprolide. The results demonstrated that the patients receiving treatment with PPI-149 experienced gynaecomastia to a lesser extent than those treated with leuprolide depot.

Example 3

To prepare a sustained release LHRH antagonist formulation, a 100 ml solution of the LHRH antagonist PPI-149 was prepared by dissolving 6.25 mg/ml of PPI-149 in water, An equal sample (100 ml minimum) of USP carboxymethylcellulose sodium (CMC) (low viscosity grade, Hercules Chemical Co.) was prepared at 0.125% w/v and mixed until dissolved. Equal portions of the PPI-149 and CMC solutions were mixed (giving a CMC:peptide ratio of 0.2:1 (w/w)) and a solid material was obtained. The solid material was stirred overnight and then collected by filtration over a 0.45micron nylon filter. HPLC evaluation of the solution filtrate indicated at least 95% of the PPI-149 compound was converted to the solid complex, was removed from solution. The recovered white paste was rinsed twice with water and then transferred to a vial and dried in vacuo. Upon dying for 72 hours, 633 mg of a white powder was obtained. The solid material was then powdered in a mortar and pestle. Elemental analysis indicated 57% peptide in the complex.

Example 4

In this example, patients with stage D1 or D2 metastatic prostate cancer or patients with a rising Prostate Specific Antigen (PSA) level after radiation therapy, radical prostatectomy, or other local therapy were treated with the LHRH antagonist PPI-149 at a dosage of either 50 mg or 50–100 mg for a sustained period of time (e.g., 4 weeks, 8 weeks, or 85 days). Other patients were treated with the LHRH agonist leuprolide (LUPRON™) with or without an anti-androgen.

During the course of treatment, patients were asked to fill out a questionnaire, which probed symptoms such as the frequency, severity, and duration of hot flashes. A summary of the results for the occurence of hot flashes in patients treated for 4 weeks with either PPI-149 alone, or leuprolide in combination with the anti-androgen are summarized below in Table I:

TABLE I

Occurrence of Hot Flashes

| Number of hot flashes/week | 0 | 1–4 | 5–>10 | p |
|---|---|---|---|---|
| Leuprolide = anti-androgen (n = 31) | 43% | 33% | 26% | .048 |
| PPI-149 (n = 199) | 61% | 19% | 20% | .048 |

A summary of the results for the severity, of hot flashes in patients treated for 4 weeks with either PPI-149 alone, or leuprolide in combination with the anti-androgen are summarized below in Table II:

TABLE II

Severity of Hot Flashes

| Severity of hot flashes | 0 | mild–moderate | moderate–severe | p |
|---|---|---|---|---|
| Leuprolide ± anti-androgen (n = 31) | 42% | 55% | 3% | .003 |
| PPI-149 (n = 199) | 62% | 38% | 0% | .003 |

A summary of the results for the duration of hot flashes in patients treated for 4 weeks with either PPI-149 alone, or leuprolide in combination with the anti-androgen are summarized below in Table III:

TABLE III

Duration of Hot Flashes

| Duration of hot flashes | 0 minutes | 0–2 minutes | ≧5 minutes | p |
|---|---|---|---|---|
| Leuprolide ± anti-androgen (n = 31) | 42% | 32% | 26% | .003 |
| PPI-149 (n = 199) | 61% | 31% | 8% | .003 |

These data demonstrate that during the first 4 weeks of treatment, patients treated with the LHRH antagonist PPI-149 alone experienced hot flashes less frequently than patients treated with leuprolide and anti-androgen. Moreover, the hot flashes in patients treated with PPI-149 alone were less severe and lasted for a shorter period of time than the hot flashes in patients treated with leuprolide and anti-androgen.

Equivalents

Those skilled in the art will recognize, or be able to ascertain using no more than routine experimentation, many equivalents to the specific embodiments of the invention described herein. Such equivalents are intended to be encompassed by the following claims.

What is claimed:
1. A method of treating a subject for gynaecomastia, comprising:
   (a) selecting a subject in need of treatment for gynaecomastia; and
   (b) administering to said subject an LHRH antagonist, thereby treating said subject for gynaecomastia.
2. A method of inhibiting gynaecomastia in a subject comprising administering to the subject an LHRH antagonist such that gynaecomastia is inhibited in the subject.
3. The method of claim 2 or 1, wherein gynaecomastia is the result of a hormonal imbalance.
4. The method of claim 2 or 1, wherein the LHRH antagonist has the structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.
5. The method of claim 2 or 1, wherein the LHRH antagonist has the structure: Ac-D-Nal$^1$, 4-Cl-D-Phe$^2$, D-Pal$^3$, Tyr$^5$, D-Asn$^6$, Lys(iPr)$^8$, D-Ala$^{10}$-LHRH.
6. The method of claim 2 or 1, wherein said subject is a human.

7. The method of claim 2 or 1, wherein the LHRH antagonist is administered to the subject by a parenteral route.

8. The method of claim 2 or 1, wherein the LHRH antagonist is administered to the subject by intramuscular, intradermal or subcutaneous injection.

9. The method of claim 2 or 1, wherein the LHRH antagonist is administered to the subject in a pharmaceutically acceptable formulation.

10. The method of claim 9, wherein the pharmaceutically acceptable formulation comprises a lipid-based formulation.

11. The method of claim 9, wherein the pharmaceutically acceptable formulation comprises a polymeric matrix.

12. The method of claim 9, wherein the pharmaceutically acceptable formulation comprises the LHRH antagonist in an insoluble complex with an anionic carrier macromolecule.

13. The method of claim 2 or 1, wherein the LHRH antagonist is administered at a dosage of about 15–300 $\mu$g/kg/day.

14. The method of claim 2 or 1, wherein the LHRH antagonist is administered at a dosage of about 15–200 $\mu$g/kg/day.

15. The method of claim 2 or 1, wherein the LHRH antagonist is administered at a dosage of about 15–100 $\mu$g/kg/day.

16. The method of claim 2 or 1, wherein the LHRH antagonist is administered continuously using a sustained-release formulation.

17. The method of claim 2 or 1, wherein the LHRH antagonist is administered to the subject in combination with at least one other therapeutic agent.

* * * * *